United States Patent
Kollias et al.

(10) Patent No.: US 8,725,236 B2
(45) Date of Patent: May 13, 2014

(54) METHOD FOR DEMONSTRATING PRE-EMERGENT PIMPLES

(75) Inventors: Nikiforos Kollias, Skillman, NJ (US); Georgios N. Stamatas, Issy-les-Moulienaux (FR)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 1137 days.

(21) Appl. No.: 11/681,330

(22) Filed: Mar. 2, 2007

(65) Prior Publication Data

US 2007/0237374 A1    Oct. 11, 2007

Related U.S. Application Data

(60) Provisional application No. 60/778,199, filed on Mar. 2, 2006.

(51) Int. Cl.
*A61B 6/00* (2006.01)

(52) U.S. Cl.
USPC ........... 600/476; 600/473; 600/475; 600/477; 382/128; 514/859

(58) Field of Classification Search
USPC ......................................... 600/473, 475–477
See application file for complete search history.

(56) References Cited

U.S. PATENT DOCUMENTS

| | | | |
|---|---|---|---|
| 5,760,407 A | 6/1998 | Margosiak et al. | |
| 6,887,260 B1 * | 5/2005 | McDaniel | 607/88 |
| 7,974,670 B2 | 7/2011 | Souta et al. | |
| 2003/0086703 A1 | 5/2003 | Kollias et al. | |
| 2003/0086712 A1 | 5/2003 | Merola et al. | |
| 2003/0138249 A1 | 7/2003 | Merola et al. | |
| 2005/0049467 A1 | 3/2005 | Stamatas et al. | |
| 2005/0270528 A1 | 12/2005 | Geshwind et al. | |
| 2007/0002479 A1 | 1/2007 | Menke et al. | |
| 2007/0005393 A1 | 1/2007 | Cole et al. | |

FOREIGN PATENT DOCUMENTS

| | | |
|---|---|---|
| EP | 1 512 373 A | 3/2005 |
| JP | 11076173 A | 3/1999 |
| JP | 2002-200050 A | 7/2002 |
| WO | WO 2005/079661 A | 9/2005 |

OTHER PUBLICATIONS

Nikiforos et al. "Optical Non-Invasive Approaches to Diagnosis of Skin Diseases", Optical Diagnostics in Dermatology, vol. 7, No. 1, Dec. 2002.*

(Continued)

*Primary Examiner* — Unsu Jung
*Assistant Examiner* — Joseph M Santos
(74) *Attorney, Agent, or Firm* — Joel Rothfus

(57) ABSTRACT

A method for demonstrating pre-emergent pimples is disclosed. The method includes providing a camera having a 25 mm macro lens and a linear polarizing filter including from 10 to 50 narrow band filters in the spectral range of 400-970 nm, and a light source having a linear polarizer oriented vertical to a polarization plane of the camera polarizer; taking a sequence of images of the face of a subject with the camera; creating an erythema map of the imaged area using oxyhemoglobin values at each corresponding pixel; taking a visible-light image of the face of the subject; and comparing the images to see pre-emergent pimples. The method enables consumers to see pre-emergent pimples and treat them, which results in preventing the pimples from emerging or reducing the emergence of the pimples.

7 Claims, 1 Drawing Sheet
(1 of 1 Drawing Sheet(s) Filed in Color)

(56) References Cited

OTHER PUBLICATIONS

Stamatas et al, "Hyperspectral Image Acquisition and Analysis of Skin", *Proceedings of the SPIE*, SPIE, Bellingham, VA, US, vol. 4959, 2003, pp. 77-82 (XP002303194).

CRI-INC: "VariSpec Liquid Crystal Tunable Filters", Brochure [Online], Jun. 17, 2006, retrieved from the internet: URL http://www.cri-inc.com/files/VariSpec_Brochure.pdf [retrieved on Jul. 20, 2007] (XP002443554).

Kollias et al, "Quantitative Assessment of UV-induced Pigmentation and Erythema", *Photo-dermatology*, vol. 5(1), pp. 53-60 (Feb. 1988).

Stamatas et al, "Blood Stasis Contributions to the Perception of Skin Pigmentation", *Journal of Biomedical Optics*, vol. 9, pp. 315-322 (2004).

Kollias, et al., "Fluorescence spectroscopy of skin", *Vibrational Spectroscopy*, vol. 28, (2002) pp. 17-23.

Lucchina, et al., "Fluorescence photography in the evaluation of acne", *Journal of the American Academy of Dermatology*, (Jul. 1996) vol. 35, No. 1, pp. 58-63.

Pagnoni, et al., "Digital fluorescence photography can assess the suppressive effect of benzoly peroxide on *Propionibacterium acnes*", *Journal of the American Academy of Dermatology*, (Nov. 1999) vol. 41, No. 5, Part 1, pp. 710-716.

Phillips, et al., "Polarized light photography enhances visualization of inflammatory lesions of acne vulgaris", *Journal of the American Academy of Dermatology*, (Dec. 1997) vol. 37, No. 6, pp. 948-952.

* cited by examiner

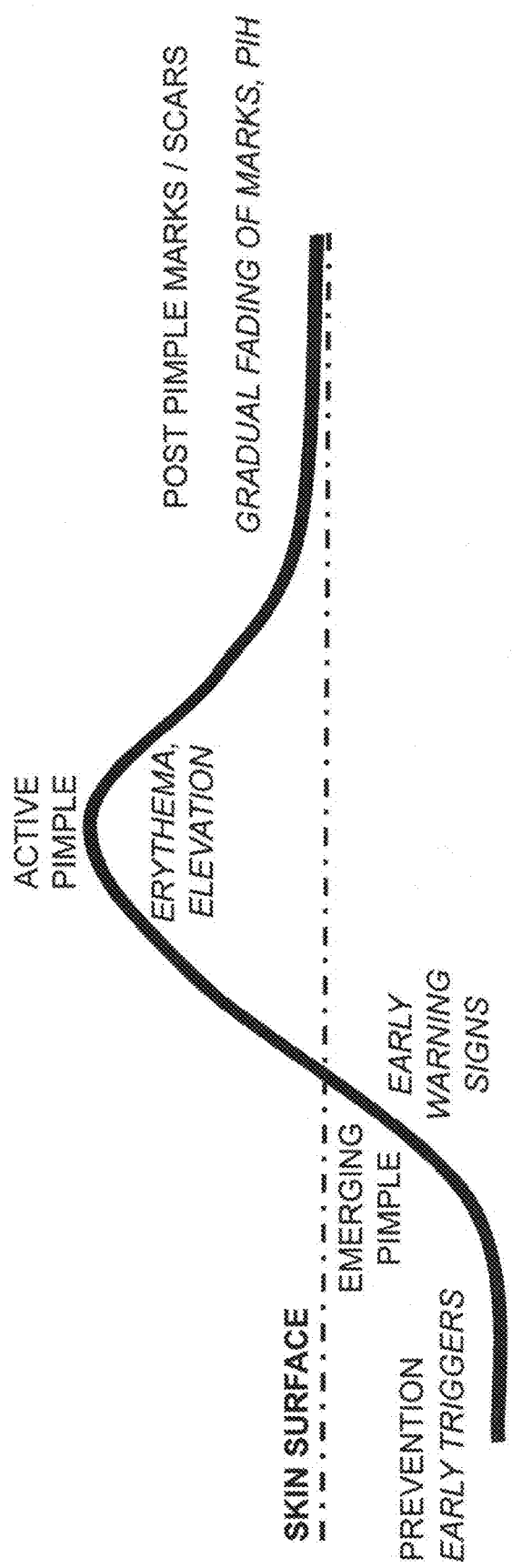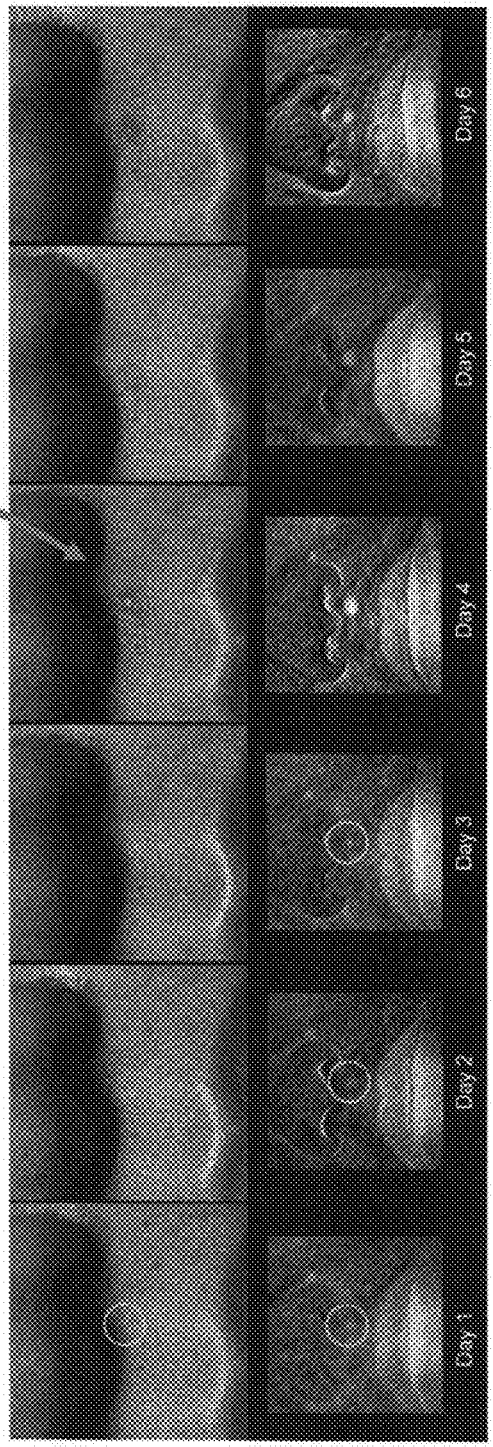

METHOD FOR DEMONSTRATING PRE-EMERGENT PIMPLES

CROSS-REFERENCE TO RELATED APPLICATIONS

This application claims priority to U.S. Ser. No. 60/778199, filed Mar. 2, 2006, the entire disclosure of which is hereby incorporated by reference.

BACKGROUND OF THE INVENTION

1. Field of the Invention

The present invention relates to a method for demonstrating pre-emergent pimples. The method utilizes spectral imaging technology. This method is useful for diagnosing where skin needs treatment to prevent the emergence of a pimple and to evaluate where the skin has improved as a result of treatment.

2. Description of the Prior Art

Clinical manifestations of inflammatory acne lesions can be described as visible (erythema), tactile (edema), and sensory (itch, soreness, discomfort). However, acne lesions begin to form in the pilosebaceous unit days to weeks before they become visible on the skin ("pre-emergent pimples"). Patients often sense an emerging inflammatory lesion as a slight soreness, discomfort, skin hardening, itching, or tingling under the skin where the lesion is forming. It is very beneficial for acne sufferers to treat lesions before they emerge to lessen and prevent any physiological sequelae of acne (i.e. residual marks, scarring, post-inflammatory hyperpigmentation) or psychological aspects of acne (i.e. embarrassment, social discomfort). Therefore, there is a need for a method of demonstrating pre-emergent pimples.

It is known to take images of the skin under various lighting conditions and through various filters to demonstrate wrinkles, acne, skin pigmentation and the like. United States Patent Application publication 20050270528 teaches various applications for multispectral and/or hyperspectral imaging. A multispectral and/or hyperspectral image of skin is disclosed in the application.

SUMMARY OF THE INVENTION

The present invention provides a method for demonstrating pre-emergent pimples including: providing a camera having a linear polarizing filter with from 4 to 50 narrow band filters in the spectral range of 400-1000 nm, and a light source having a linear polarizer oriented vertical to a polarization plane of the camera polarizer; taking a sequence of images of the face of a subject with the camera; creating an erythema map of the imaged area using oxy-hemoglobin values at each corresponding pixel; taking a visible-light image of the face of the subject; and comparing the images to detect pre- emergent pimples.

The present invention also provides a method of preventing or minimizing the emergence of pimples including: providing a camera having a linear polarizing filter including from 10 to 50 narrow band filters in the spectral range of 400-1000 nm, and a light source having a linear polarizer oriented vertical to a polarization plane of the camera polarizer; taking a sequence of images of the face of a subject with the camera; creating an erythema map of the imaged area using oxy-hemoglobin values at each corresponding pixel; taking a visible-light image of the face of the subject; comparing the images to see pre-emergent pimples; and applying an anti-acne composition to the pre-emergent pimple to prevent or minimize the emergence of pimples.

The present invention also provides a method for demonstrating pre-emergent pimples including sequential acquisition of images filtered at characteristic narrow spectral bands. The images constitute a spectral image cube and each pixel of the image corresponds to a reflectance spectrum of the imaged skin area. The spectra can be analyzed to evaluate the relative concentrations of skin chromophores, including melanin, oxy-hemoglobin, and deoxy-hemoglobin. An erythema map of the imaged area can be composed using the oxy-hemoglobin values at each corresponding pixel. Inflammatory lesions demonstrate increased levels of oxy-hemoglobin compared to surrounding skin. The relative intensity and size of erythema present in a lesion can be determined. Comparing the erythema map to traditional visible-light images, areas of emerging lesions can be identified. Emerging lesions are apparent in the erythema map, but not in the visible-light images. This method allows for better specificity—identifies only lesions that have an erythema aspect. Other imaging techniques detect hyperpigmented lesions or scarring and shadowing, which makes it more difficult to discern whether there is an active lesion or a residual mark from a past lesion.

BRIEF DESCRIPTION OF THE DRAWINGS

The patent or application file contains at least one drawing executed in color. Copies of this patent with color drawing(s) will be provided by the Patent and Trademark Office upon request and payment of necessary fee.

FIG. 1 is a timeline with an associated series of color photographs and corresponding filtered polarized images identifying a cycle of pimple emergence and fading.

DETAILED DESCRIPTION OF PREFERRED EMBODIMENTS

The present invention utilizes a spectral imaging system to generate images of skin. One suitable spectral imaging system includes a custom-made camera (FORTH Photonics, Athens, Greece) with a 25 mm macro lens and a linear polarizing filter capable of multispectral (up to about 30 narrow band filters) and/or hyperspectral (greater than about 30 narrow band filters) imaging (hereafter, both multispectral and hyperspectral are collectively "ms/hs"). The camera contains multiple narrow band filters, for example from 4 to 50 narrow band filters in the spectral range of 400-1000 nm. A particularly useful camera for the present invention contains 30 narrow-band filters in the spectral range of 400-970 nm. It is important to have at least 4 filters in the spectral range of 560-730 nm. The settings for the image acquisition including filter selection, exposure time, and camera gain are preferably controlled through computer software.

A linearly polarized light source is utilized in the present invention. One suitable linearly polarized light source is the v600, Syris, Gray, Me. Preferably, the polarization plane is positioned vertical to the polarization plane of the camera polarizer. Thus, artifacts due to specular reflection may be minimized.

A head restraint may be used for reproducible positioning of the subjects. The distance from the camera to the subject to be imaged may range between 60 and 100 cm. The field of view may be set at 16 cm×12 cm with a resolution of 0.156 mm/pixel for both x and y axes.

Image analysis requires pre-processing of the raw data according to the following method:

Image Pre-Processing Method

First alignment of the ms/hs images is performed using a phase correction algorithm as recognized by one of ordinary skill in the art. Second, absorption spectra are calculated for each pixel as the negative logarithm of the image of interest to the image at 850 nm, where water, melanin, and hemoglobin absorptions are negligible. Normalization to the image at 850 nm also results in minimizing artifacts due to contours. Finally, chromophore maps are calculated based on algorithms developed for Diffuse Reflectance Spectrometry (Kollias N, Baqer AH: Quantitative assessment of UV-induced pigmentation and erythema. Photodermatol 5:53-60, 1988; Stamatas GN, Kollias N: Blood stasis contributions to the perception of skin pigmentation. J Biomed Opt 9:315-322, 2004; US Pat. App. No. 2005/0049467A1 "Method for Assessing Pigmented Skin") the disclosures of which are herein incorporated by reference. Briefly, the absorbance spectrum is calculated for each pixel as the negative logarithm of the ratio of the remittance spectrum of that pixel to the remittance spectrum of the corresponding pixel of a white target ms/hs image. Pigment is evaluated from the absorbance curve as the slope of the fitted straight line over the wavelength range of 630-730 nm, after correction for the contribution of deoxy-Hb absorption in this region. Then the curve is corrected for the pigment absorption and finally, the corrected spectrum is fitted to the oxy-Hb and deoxy-Hb absorption spectra in the range of 550-580 nm, where they exhibit local maxima.

The method of the present invention is useful for evaluating the skin condition and for demonstrating the effectiveness of cosmetic products. For example, images may be taken prior to and after application of an anti-acne cream. The images enable the consumer to apply anti-acne products to areas containing pre-emergent pimples, thereby preventing or minimizing the emergence of pimples.

In one embodiment of the invention, areas containing pre-emergent pimples are identified through ms/hs imaging, and anti-acne agents. What is meant by an anti-acne agent is an compound that has been approved by the U.S. Food and Drug Administration for the topical treatment of acne. Examples of anti-acne agents include, but are not limited to, salicylic acid, benzoyl peroxide, sulphur, retinoic acid, candida bombicola/glucose/methyl rapeseedate ferment, peat water, resorcinol, silt, peat, permethin, azelaic acid, clindamycin, adapalene, erythromycin, sodium sulfacetamide, and combinations thereof.

EXAMPLE 1

Five male and female volunteers ages 18-40, Fitzpatrick Skin Type I-IV, with mild inflammatory acne participated in the study. The qualified volunteers had a history of experiencing at least 2 new inflammatory lesions per week (through self-report). No treatment usage or change in current skincare regimens was allowed for the duration of the study.

High-resolution visible illumination images and multi-spectral images were acquired daily Monday through Friday for 2 weeks. The spectral imaging system consisted of a custom-made ms/hs camera (FORTH Photonics, Athens, Greece) with a 25 mm macro lens and a linear polarizing filter. The camera contained 30 narrow-band filters in the spectral range of 400-970 nm. The settings for the image acquisition including filter selection, exposure time, and camera gain were controlled through computer software. A linearly polarized light source was used (v600, Syris, Gray, Me.) with its polarization plane positioned vertical to the polarization plane of the camera polarizer. Thus, artifacts due to specular reflection were minimized. A custom-built head restraint was used for reproducible positioning of the subjects. The distance from the camera to the subject ranged between 60 and 100 cm. The field of view was set at 16 cm×12 cm with a resolution of 0.156 mm/pixel for both x and y axes.

The images were subjected to the Imaging Pre-Processing Method, above. By combining visible illumination imaging with chromophore maps obtained from ms/hs imaging (FIG. 1), it was demonstrated that emerging lesions can be detected and evaluated. In the visible images, no lesion was seen until day 4. In the oxy-Hb maps from spectral imaging, the lesion were detected as early as 3 days before the lesion were visible. The amount of oxy-Hb was quantified by the number of pixels and intensity of the reflectance. In all other subjects, it was possible to identify lesions 1 to 3 days prior to the lesion surfacing.

EXAMPLE 2

Having developed a methodology to identify and quantify sub-clinical inflammatory acne lesions, the method was used in a larger scale clinical study. The clinical study was conducted with the following objectives: 1) To compare the results of the imaging methods with subject self-assessments, and 2) to evaluate the efficacy of a novel 2% salicylic acid composition and a 10% benzoyl peroxide (10% BPO) composition in the treatment of emerging acne.

Forty-one male and female subjects ages 12-30, Fitzpatrick Skin Type I-IV, with mild to moderate acne completed the study. To qualify, subjects must have had a history of experiencing 2 new inflammatory lesions per week (through self-report). Subjects were randomly assigned to one of 2 treatment groups:

a) 10% Benzoyl Peroxide treatment (n=21), and
b) 2% salicylic acid product treatment (n=20).

Subjects applied their assigned treatments full-face, twice daily for 6 weeks. Visible illumination digital imaging was performed at baseline, days 7-13*, week 5 and week 6. Multi-spectral imaging was performed at days 7-13*, week 5 and week 6. Self-assessment questionnaires at were given at baseline, days 7-13, week 5, and week 6.* The consecutive daily measurements were done in order to monitor emerging lesions.

A Tripix camera (ElectroImage Inc., Great Neck, N.Y.) was modified to include filters with spectral bands relative to skin chromophores. The narrow-band interference filters used were centered at 560, 580, 630, and 700 nm with a band pass of 10 nm. A 12-36 mm macro lens was fitted on the camera and a linear polarizing filter was placed in front of the lens. The camera resolution was 1280×1024 pixels. The settings for the image acquisition including filter selection, exposure time, and camera gain were controlled through computer software. A linearly polarized light source was used (v600, Syris, Gray, Me.) with its polarization plane positioned vertical to the polarization plane of the camera polarizer. Thus, artifacts due to specular reflection were minimized. A custom-built head restraint was used for reproducible positioning of the subjects.

Again, the images were subjected to the Imaging Pre-Processing Method, above.

During the study, participants responded to two statements that address emerging acne. Participants in both groups indicated that the treatments were efficacious in treating emerging acne. Emerging acne lesions were visualized in the ms/hs images, and the lesions resolved without ever appearing in the visible illumination images. Therefore, this method effectively documents the resolution of sub-clinical inflammatory lesions.

What is claimed is:

1. A method of reducing the emergence of pimples comprising the steps of:
   a) using a hyperspectral camera to acquire sequential images of skin filtered at characteristic narrow spectral bands, the images constituting a spectral image cube and each area of the image corresponds to a reflectance spectrum of the imaged skin area, the hyperspectral camera comprising a linear polarizing filter comprising from 4 to 50 narrow band filters in the spectral range of 400-1000 nm with at least 4 filters in the spectral range of 560-730 nm, and a light source having a linear polarizer oriented vertical to a polarization plane of the camera polarizer;
   b) analyzing the acquired images by calculating absorption spectra for acquired pixel values in the image as the negative logarithm of a ratio of the image at each wavelength to the corresponding image of a white reflectance standard at the corresponding wavelength to determine relative concentrations of at least one skin chromophore;
   c) creating an erythema map of the imaged skin using the concentration value of the at least one skin chromophore at each corresponding area of the image; and
   d) comparing the erythema map to at least one broad spectrum, visible-light image of the imaged skin area to identify any area of pre-emergent pimples not evident in the visible-light image; and e) applying a composition to the pre-emergent lesion to reduce the emergence of pimples.

2. The method of claim 1, wherein the hyperspectral camera comprises a 25 mm macro lens.

3. The method of claim 1, wherein the linear polarizing filter comprises from 30 to 50 narrow band filters in the spectral range of 400 nm to 970 nm.

4. The method of claim 1, wherein the reflectance spectrum is determined for each pixel of the each image.

5. The method of claim 1, wherein the erythema map of the imaged area is created using the skin chromophore concentration values at each corresponding pixel of the image.

6. The method of claim 1, wherein the at least one skin chromophore is selected from the group consisting of melanin, oxy-hemoglobin, deoxy-hemoglobin, and combinations thereof.

7. The method of claim 6, wherein composition comprises an anti-acne agent.

* * * * *